(12) United States Patent
Murakami et al.

(10) Patent No.: US 12,416,746 B2
(45) Date of Patent: Sep. 16, 2025

(54) STACKED LENS, OPTICAL UNIT, ENDOSCOPE, AND METHOD OF MANUFACTURING OPTICAL UNIT

(71) Applicant: OLYMPUS CORPORATION, Tokyo (JP)

(72) Inventors: Kazuhiro Murakami, Nagano (JP); Kensuke Suga, Nagano (JP); Jumpei Yoneyama, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 350 days.

(21) Appl. No.: 18/122,954

(22) Filed: Mar. 17, 2023

(65) Prior Publication Data
US 2023/0233060 A1 Jul. 27, 2023

Related U.S. Application Data

(63) Continuation of application No. PCT/JP2021/010651, filed on Mar. 16, 2021.

(51) Int. Cl.
G02B 23/24 (2006.01)
G02B 3/00 (2006.01)
G02B 13/00 (2006.01)
A61B 1/00 (2006.01)

(52) U.S. Cl.
CPC ......... *G02B 3/0025* (2013.01); *G02B 3/0062* (2013.01); *G02B 13/0085* (2013.01); *G02B 23/243* (2013.01); *G02B 23/2484* (2013.01); *A61B 1/00096* (2013.01)

(58) Field of Classification Search
CPC .......... G02B 3/0025; G02B 3/0062; G02B 13/0085; G02B 23/243; G02B 23/2484; G02B 7/02; A61B 1/00096; A61B 1/051; A61B 1/0011; H04N 23/555; H10F 39/12
USPC ........................................... 359/754
See application file for complete search history.

(56) References Cited

U.S. PATENT DOCUMENTS

| | | | |
|---|---|---|---|
| 2013/0107113 A1* | 5/2013 | Tazoe | G02B 7/021 348/374 |
| 2013/0301140 A1* | 11/2013 | Matsuno | G02B 5/005 359/619 |
| 2013/0340234 A1 | 12/2013 | Iwasaka et al. | |
| 2019/0260917 A1 | 8/2019 | Yamamoto et al. | |
| 2019/0384037 A1 | 12/2019 | Fleger et al. | |
| 2020/0124826 A1* | 4/2020 | Kitsunezuka | H04N 23/55 |

(Continued)

FOREIGN PATENT DOCUMENTS

| | | |
|---|---|---|
| CN | 1467524 A | 1/2004 |
| CN | 103443683 A | 12/2013 |

(Continued)

OTHER PUBLICATIONS

International Search Report dated May 25, 2021 received in PCT/JP2021/010651.

*Primary Examiner* — William R Alexander
(74) *Attorney, Agent, or Firm* — Scully, Scott, Murphy & Presser, P.C.

(57) ABSTRACT

A stacked lens includes: a first optical device; a second optical device disposed on an optical axis of the first optical device; and an adhesive layer bonding the first optical device and the second optical device and including a projection projecting outside a side surface of the first optical device and a side surface of the second optical device.

17 Claims, 10 Drawing Sheets

(56) References Cited

U.S. PATENT DOCUMENTS

| | | | | |
|---|---|---|---|---|
| 2020/0223781 | A1* | 7/2020 | Someya | C07C 69/602 |
| 2020/0249473 | A1* | 8/2020 | Genda | G02B 7/025 |
| 2020/0310015 | A1* | 10/2020 | Oyama | G02C 7/104 |
| 2020/0348789 | A1* | 11/2020 | Chen | G09G 3/03 |
| 2020/0384723 | A1* | 12/2020 | Gao | B32B 3/30 |
| 2020/0391434 | A1* | 12/2020 | Padiou | B29D 11/00432 |
| 2020/0391486 | A1* | 12/2020 | Saito | B29C 48/02 |
| 2020/0410208 | A1* | 12/2020 | Thothadri | G02F 1/133305 |

FOREIGN PATENT DOCUMENTS

| | | | |
|---|---|---|---|
| JP | 2004133328 | A | 4/2004 |
| JP | 6523587 | B1 | 6/2019 |
| WO | 2011/062209 | A1 | 5/2011 |
| WO | 2018/087872 | A1 | 5/2018 |
| WO | 2018/146065 | A1 | 8/2018 |

* cited by examiner

STACKED LENS, OPTICAL UNIT, ENDOSCOPE, AND METHOD OF MANUFACTURING OPTICAL UNIT

CROSS REFERENCE TO RELATED APPLICATION

This application is a continuation application of PCT/JP 2021/010651 filed on Mar. 16, 2021, the entire contents of which are incorporated herein by this reference.

BACKGROUND OF THE INVENTION

1. Field of the Invention

Embodiments of the present invention relate to a stacked lens including a plurality of optical devices stacked with an adhesive layer in between, an optical unit including the stacked lens, an endoscope including the optical unit, and a method of manufacturing the optical unit.

2. Description of the Related Art

Optical units are used for an image pickup optical system for an image pickup unit and an illumination optical system for an illumination unit. To downsize an optical unit, a stacked lens including a plurality of optical devices stacked with an adhesive layer in between has been suggested. The stacked lens is manufactured by cutting a stacked wafer including a plurality of optical wafers bonded with an adhesive agent.

International Publication No. 2018/087872 discloses an endoscope where a stacked lens, a side surface of which includes a recessed portion, is disposed in a distal end member. In inserting the stacked lens into the distal end member for fixation, a position offset is prevented by bringing the recessed portion of the side surface into contact with a projection of the distal end member.

SUMMARY OF THE INVENTION

A stacked lens according to an embodiment of the present invention includes: a first optical device; a second optical device disposed on an optical axis of the first optical device; and a first adhesive layer bonding the first optical device and the second optical device and including a first projection projecting outside an outer peripheral surface of each of the first optical device and the second optical device, the outer peripheral surface being along the optical axis.

An optical unit according to an embodiment of the present invention includes: a stacked lens including: a first optical device; a second optical device disposed on an optical axis of the first optical device; and a first adhesive layer bonding the first optical device and the second optical device and including a first projection projecting outside an outer peripheral surface of each of the first optical device and the second optical device, the outer peripheral surface being along the optical axis; and a first frame member in which the stacked lens is housed and that has an inner surface including a first positioning member, the first projection being in contact with the first positioning member.

An endoscope according to an embodiment of the present invention includes an insertion section and an optical unit disposed in a distal end portion of the insertion section, the optical unit including: a stacked lens including: a first optical device; a second optical device disposed on an optical axis of the first optical device; and a first adhesive layer bonding the first optical device and the second optical device and including a first projection projecting outside an outer peripheral surface of each of the first optical device and the second optical device, the outer peripheral surface being along the optical axis; and a frame member in which the stacked lens is housed and that has an inner surface including a positioning member, the first projection being in contact with the positioning member.

A method of manufacturing an optical unit according to an embodiment of the present invention includes: producing a stacked wafer including a first optical wafer including a plurality of first optical devices, a second optical wafer including a plurality of second optical devices, and an adhesive layer between the first optical wafer and the second optical wafer; cutting the stacked wafer using a dicing blade to produce a stacked lens, the stacked lens including one of the first optical devices, one of the second optical devices, and a first adhesive layer including a projection projecting outside a cut surface; and housing the stacked lens in a frame member having an inner surface including a positioning member in a state where the projection is in contact with the positioning member.

DETAILED DESCRIPTION OF THE PREFERRED EMBODIMENTS

First Embodiment

Figure 1:
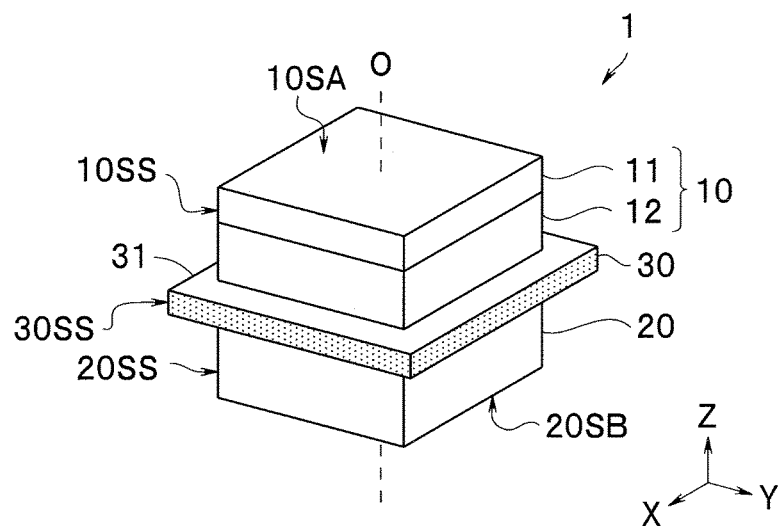
FIG. 1 is a perspective view of a stacked lens of a first embodiment.
Figure 2:
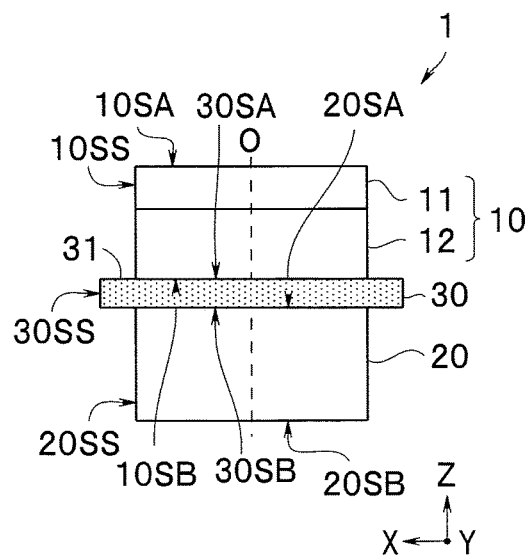
FIG. 2 is a side view of the stacked lens of the first embodiment.
Figure 3:
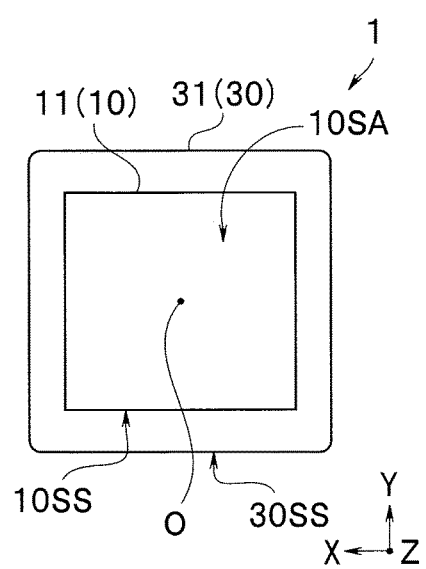
FIG. 3 is a top view of the stacked lens of the first embodiment.

As illustrated in FIG. 1 to FIG. 3, a stacked lens 1 of a present embodiment includes a first optical device 10, a second optical device 20 disposed on an optical axis of the first optical device 10, and a first adhesive layer 30 (hereinafter, referred to as an "adhesive layer 30") bonding the first optical device 10 and the second optical device 20.

Note that drawings of the embodiments and the like are schematic views. A relationship between a thickness and a width of each portion, a ratio between respective thicknesses of portions, and the like are different from actual ones. A relationship and a ratio between respective dimensions of some portions may be different even among the drawings. In addition, illustration and assignment of reference numbers are omitted for some components.

The first optical device 10, which is in a shape of rectangular parallelepiped, has a first principal surface 10SA and four side surfaces 10SS. The second optical device 20, which is in a shape of a rectangular parallelepiped, has a second principal surface 20SB and four side surfaces 20SS. The adhesive layer 30 is a resin layer bonding a surface of the first optical device 10 opposite the first principal surface 10SA and a surface of the second optical device 20 opposite the second principal surface 20SB. The first principal surface 10SA and the second principal surface 120SB are substantially in the same shape and have substantially the same surface area. That is, the four side surfaces 10SS of the first optical device 10 are flush with the respective four side surfaces 20SS of the second optical device 20. In other words, the first optical device 10 and the second optical device 20 overlap as observed in a direction from the first principal surface 10SA of the stacked lens 1.

The first optical device 10 is a hybrid lens device, where a resin lens 12 is disposed on a glass device 11. However, in the drawings, the resin lens 12 is illustrated as a flat plate and the first optical device 10 and the second optical device 20 are illustrated as being filled with the adhesive layer 30 with no gap between. The second optical device 20 is made of a colorless and transparent flat glass but may include a colored and transparent filter or glass lens.

Respective four side surfaces 30SS of the adhesive layer 30 project from the respective four side surfaces loss of the first optical device 10 and the respective four side surfaces 20SS of the second optical device 20. That is, the adhesive layer 30 includes an elongated protrusion, or first projection 31 (hereinafter, referred to as a "projection 31"), not interposed between the first optical device 10 and the second optical device 20. As illustrated in FIG. 3, the projection 31 surrounds the first optical device 10 (the first principal surface 10SA) and has an outline substantially in a shape of a quadrilateral picture frame as observed in the direction from the first principal surface 10SA of the stacked lens 1.

In other words, the adhesive layer 30 has an inner peripheral region bonding the first optical device 10 and the second optical device 20 and an outer peripheral region in a form of the projection 31 projecting outside the four side surfaces of the first optical device 10 and the four side surfaces of the second optical device 20. That is, the projection 31 projects outside the four side surfaces 10SS and the four side surfaces 20SS, which are outer peripheral surfaces of the first optical device 10 and the second optical device 20 along an optical axis O.

A thickness of the adhesive layer 30, that is, a thickness of the projection 31, is in a range from 50 μm to 100 μm. In addition, the adhesive layer 30 is made of soft resin having a smaller modulus of elasticity E than the first optical device 10 and the second optical device 20. For example, the modulus of elasticity E of the adhesive layer 30 is preferably in a range from 0.1 MPa to 4 MPa.

For example, in holding the stacked lens 1 with tweezers the soft projection 31 serves as a slip resistance; therefore, the stacked lens 1 is user-friendly.

The modulus of elasticity E is measured by tensile dynamic viscoelastic measurement (DMA). After a sample is clamped to a measurement head, stress is applied to the 25-degree-C. sample from a load generation section through a probe. The stress was provided as a sinusoidal force with a predetermined frequency and set such that a strain amplitude of the sample became constant. A deformation of the sample caused by the sinusoidal force is detected by a deformation detection section. The modulus of elasticity was calculated from the stress applied to the sample and the detected strain (for example, JIS K6394).

At a projection amount of the projection 31 from the side surfaces 10SS, 20SS of 5 μm or more, a slip resistance effect is outstanding. At a projection amount of 100 μm or less, the stacked lens 1 has a small outer size in a direction orthogonal to the optical axis O.

The first optical device 10 and the second optical device 20 are optical devices configured to provide desired optical properties. For example, the optical devices may each be a hybrid lens device where resin lens devices are disposed on both sides of a glass device. That is, the adhesive layer may bond the resin lens device and the resin lens device. In addition, the adhesive layer may bond the glass device and the glass device. Note that an incoming surface of the stacked lens where light is to enter may be one of the first principal surface 10SA and the second principal surface 20SB.

<Method of Manufacturing Stacked Lens>

Description will be made on a method of manufacturing the stacked lens 1.

<Step S10> Production of Optical Wafers

Figure 4:
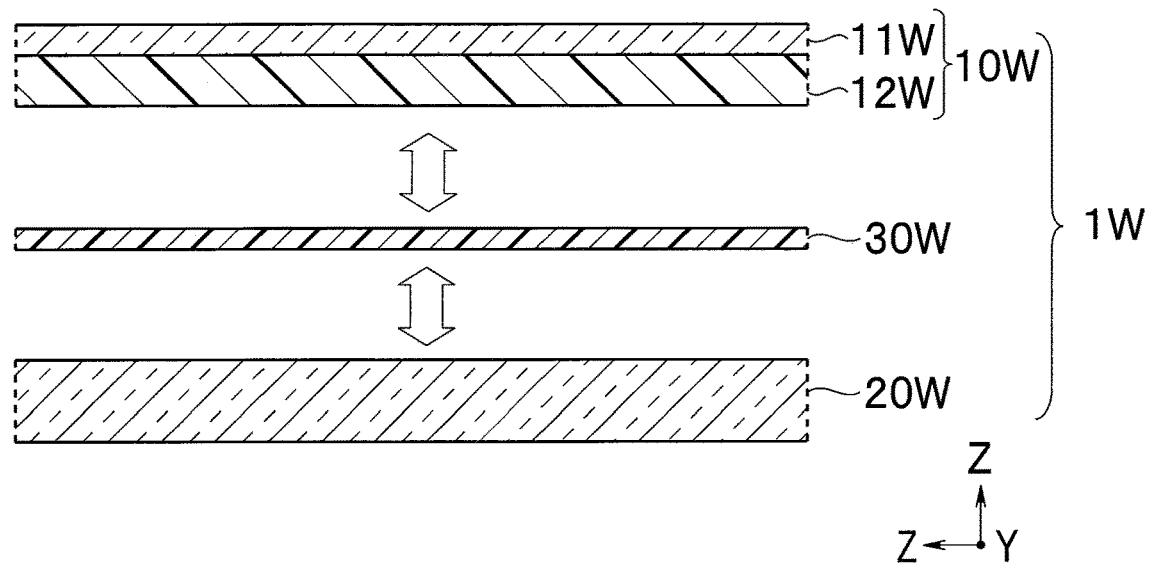
FIG. 4 is a cross-sectional view for explaining a method of manufacturing the stacked lens of the first embodiment.

A first optical wafer 10W illustrated in FIG. 4 is produced by disposing a resin layer 12W, which includes a plurality of the resin lenses 12, all over a glass wafer 11W. The second optical wafer 20W is a glass wafer.

It is preferable that the resin layer 12W be curable resin. When the curable resin externally receives an energy such as heat, ultraviolet light, or electron beam, a cross-linking reaction or a polymerization reaction progresses. The resin lens 12 is made of, for example, transparent ultraviolet curable silicone resin, epoxy resin, or acrylic resin. Note that "transparent" means that light absorption and diffusion of a material are small enough to be usable in a wavelength range to use.

For example, the resin layer 12W is produced by a die molding method including disposing uncured resin on the glass wafer 11W and applying ultraviolet light to cure the resin while pressing a die having a recessed portion with a predetermined inner surface shape against the resin. Since the inner surface shape of the die is transferred to an outer surface shape of the resin lens, the die molding method enables easily producing even an aspheric lens.

The resin layer 12W including the resin lenses 12 may be produced by patterning a resin layer by a photolithography technique or a metal masking technique and then performing an appropriate heat treatment. Alternatively, the resin layer 12W may be produced by an ink jet technique.

The first optical wafer 10W and the second optical wafer 20W may each be transparent resin as a whole or may each be a combination of glass and resin as appropriate. That is, the first optical wafer 10W and the second optical wafer 20W may be composed of a plurality of layers made of the same material or different materials. In addition, the first optical wafer 10W and the second optical wafer 20W may each be a rectangular wafer or a round wafer.

The first optical wafer 10W and the second optical wafer 20W only have to have respective light transmissive light path regions. For example, a light blocking aperture film may be disposed around each of light paths.

<Step S20> Production of Stacked Wafer

As illustrated in FIG. 4, an adhesive agent 30W is applied between the first optical wafer 10W and the second optical wafer 20W. By virtue of the adhesive layer 30 formed by curing the adhesive agent 30W, the first optical wafer 10W and the second optical wafer 20W are fixed in a direction of the optical axis O to produce the stacked wafer 1W. Predetermined known resin such as acrylic resin is used as the adhesive agent 30W constituting the adhesive layer 30. A viscosity η of the uncured adhesive agent 30W is, for example, in a range from 400 mPa·s to 3000 mPa·s.

Note that the adhesive layer 30 is made of transparent resin. However, the adhesive layer 30 at a position where the light path is not blocked may be made of a light blocking resin. In addition, the adhesive layer 30 made of the light blocking resin may serve as an aperture.

<Step S30> Dicing (Cutting of Stacked Wafer)

Figure 5:
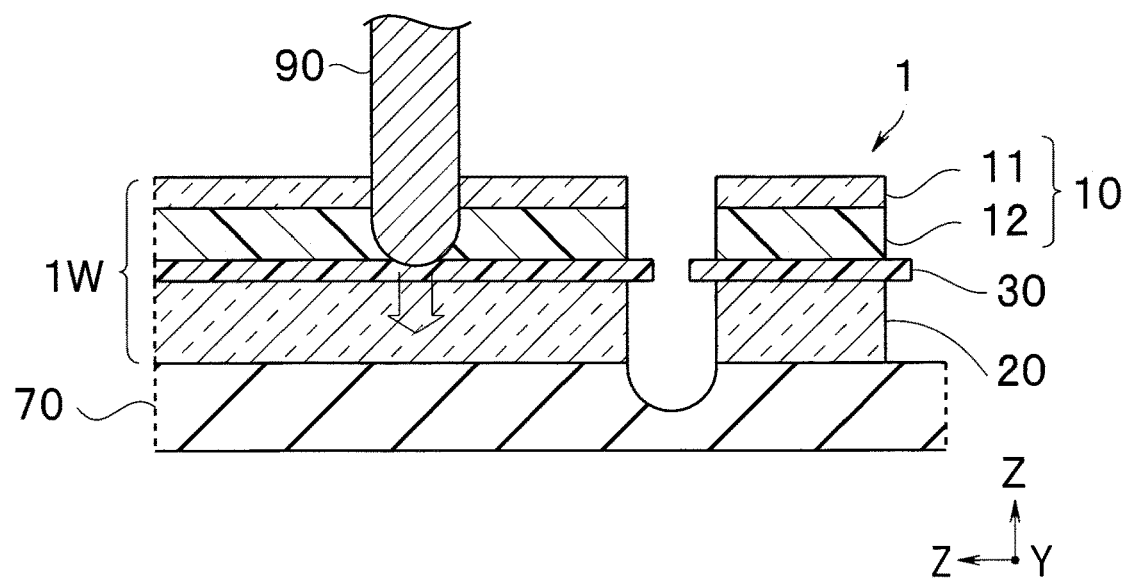
FIG. 5 is a cross-sectional view for explaining the method of manufacturing the stacked lens of the first embodiment.

As illustrated in FIG. 5, the stacked wafer 1W fixed to a dicing tape 70 is diced using a dicing blade 90 and thus divided into stacked lenses 1.

According to studies having been performed so far by the present inventors, it has been found that as a result of dividing the stacked wafer 1W into the stacked lenses 1 using the dicing blade 90 under predetermined conditions, the projection 31 of the adhesive layer 30 projects from a cut surface. A reason for the above is unknown but it is speculated that a force acting on the adhesive layer 30 in a lower direction and an external direction would be a main reason. The projection amount of the projection 31 and the number of side surfaces where the projection 31 projects could be controlled by changing a type of the adhesive agent, a thickness of the adhesive layer, the conditions for blade dicing, and the like.

The stacked lens 1 where the projection 31 of the adhesive layer 30 projects after dicing is produced by setting a type and a thickness of the adhesive layer 30. For example, the stacked lens 1 including the projection 31 with a projection amount in a range from 5 μm to 100 μm is produced by forming the adhesive layer 30 with a thickness in a range from 50 μm to 100 μm by using acrylic resin with a modulus of elasticity E in a range from 0.1 MPa to 4 MPa.

Even when the type of the adhesive layer 30 is not acrylic resin, an effect similar to the effect of the adhesive layer 30 can be achieved by, for example, adjusting the layer thickness and the modulus of elasticity.

The side surface 10SS of the first optical device 10 and the side surface 20SS of the second optical device 20, which are cut surfaces of the stacked lens 1 divided using the dicing blade 90, include a striation. The striation is likely to occur in resin of the dicing tape 70 or the like but may occur in glass or the like.

In other words, an optical device including a striation in a side surface can be considered as having been divided using the dicing blade 90.

Note that in a case where the stacked wafer 1W was divided by laser dicing or etching, no projection of the adhesive layer 30 from a side surface occurred during a dividing work.

A stacked lens including a projection projecting from a side surface of an optical device can also be produced by, for example, cutting the glass wafer 11W including glass and the second optical wafer 20W by a cutting method allowing for cutting glass but not resin, such as ultrashort pulsed-laser or hydrofluoric-acid etching, and then cutting the adhesive layer 30 with a cutting allowance smaller than a cutting allowance for glass. However, these manufacturing methods require a larger number of processes and higher manufacturing costs than the manufacturing method of the present embodiment.

For example, in holding the stacked lens 1 including the projection 31 projecting from the side surface of the optical device with tweezers, the soft projection 31 serves as a slip resistance; therefore, the stacked lens 1 is user-friendly.

<Modifications of First Embodiment>

Since stacked lenses 1A, 1B of Modifications 1, 2 of the first embodiment are similar to the stacked lens 1, the same reference sign is assigned to components with the same function and an explanation is omitted.

<Modification 1 of First Embodiment>

The stacked lens 1 of the first embodiment has a three-layer structure where the two optical devices 10, 20 are bonded by the adhesive layer 30. In contrast, the stacked lens 1A of Modification 1 of the first embodiment illustrated in FIG. 6 has a seven-layer structure including four optical devices 10A to 10D and three adhesive layers 30A to 30C.

The optical device 10A includes a glass device 11A and a resin lens 12A. The optical device 10B includes a glass device 11B and a resin lens 12B. The optical device 10C, which is disposed on an optical axis of the first optical device 10A, includes a glass device 11C and a resin lens 12C. The optical device 10D, which is disposed on the optical axis of the first optical device 10A, is a glass device 11D. Principal surfaces of the optical devices 10A to 10D are substantially in the same shape and have substantially the same surface area.

The adhesive layer 30A bonds the optical device 10A and the optical device 10B. The adhesive layer 30B bonds the optical device 10B and the optical device 10C. The adhesive layer 30C bonds the optical device 10C and the optical device 10D.

In other words, the adhesive layer 30A bonds the resin lens 12A of the optical device 10A and the resin lens 12B of the optical device 10B. The adhesive layer 30B bonds the glass device 11B of the optical device 10B and the glass device 11C of the optical device 10C.

The three adhesive layers 30A to 30C include picture-frame-shaped projections 31A to 31C projecting from the four side surfaces of the optical devices 10A to 10D, respectively.

<Modification 2 of First Embodiment>

Figure 7:
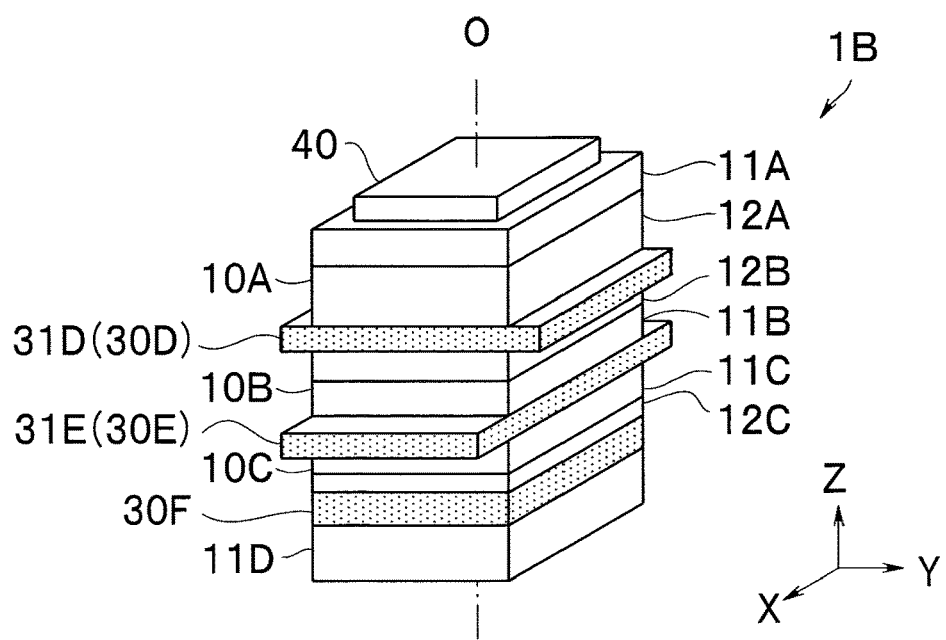
FIG. 7 is a perspective view of a stacked lens of Modification 2 of the first embodiment.

The stacked lens 1B of Modification 2 of the first embodiment illustrated in FIG. 7 includes the four optical devices 10A to 10D, three adhesive layers 30D to 30F, and an image pickup device 40 disposed on the optical axis of the first optical device 10A. The image pickup device 40 is a CCD or the like configured to receive light collected by the four optical devices 10A to 10D.

The first adhesive layer 30D bonds the optical device 10A and the optical device 10B. The second adhesive layer 30E bonds the optical device 10B and the optical device 10C. The third adhesive layer 30F bonds the optical device 10C and the optical device 10D. The principal surfaces of the optical devices 10A to 10D are substantially in the same shape and have substantially the same surface area.

The first adhesive layer 30D includes two first projections 31D projecting in a Y-axis direction. The second adhesive layer 30E includes two second projections 31E projecting in an X-axis direction. The second projections 31E project outside an outer peripheral surface (side surfaces) of each of the second optical device 10B and the third optical device 10C along the optical axis O.

In other words, the first projections 31D and the second projections 31E of the stacked lens 1B each include two projecting projections located at symmetric positions across the optical axis O. Note that the third adhesive layer 30F has no projection from the side surface of the optical member. That is, four side surfaces of the third adhesive layer 30F are flush with the respective four side surfaces of each of the optical devices 10A to 10D.

A plurality of projected images of the two first projections 31D and the two second projections 31E that are projected on an imaginary plane orthogonal to the optical axis have no overlap.

The stacked lens 1B is produced by cutting away a part of projections projecting from the four side surfaces of each of the adhesive layers 30A, 30B of the stacked lens 1A.

In addition, according to a method of manufacturing the stacked lens 1B, a plurality of image pickup devices 40 are disposed on the stacked wafer 1W, and when the stacked wafer 1W is cut, the stacked lens 1B is cut such that the stacked lens 1B includes the image pickup device 40.

The stacked lens 1B, which includes the image pickup device 40, has the same effect as the effect of the stacked lens 1.

In a case where a stacked lens includes three or more optical devices, two or more adhesive layers each bond two of the plurality of optical devices. It is sufficient if at least one of the two or more adhesive layers includes a projection projecting from side surfaces of the plurality of optical devices. In addition, the projection projecting from the side surfaces of the optical devices is not necessarily in the shape of a picture frame surrounding the optical devices.

In other words, a stacked lens of the present invention includes a plurality of optical devices and at least one adhesive layer each bonding two of the plurality of optical devices, at least one of the adhesive layers including a projection projecting outside side surfaces of the plurality of optical devices.

Note that the stacked lens may include a light-emitting device in place of the image pickup device 40.

Second Embodiment

Figure 8:
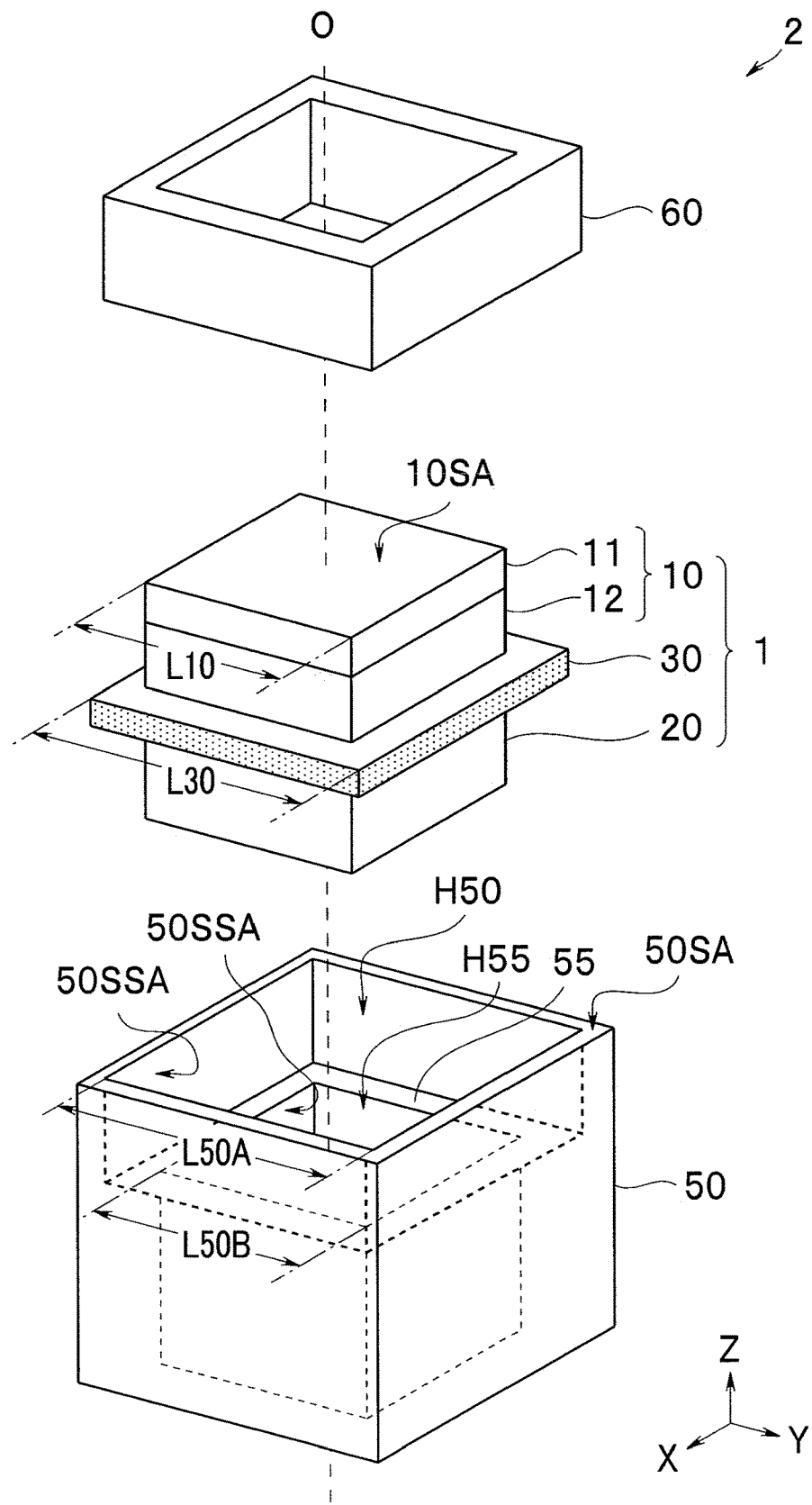
FIG. 8 is an exploded perspective view of an optical unit of a second embodiment.
Figure 9:
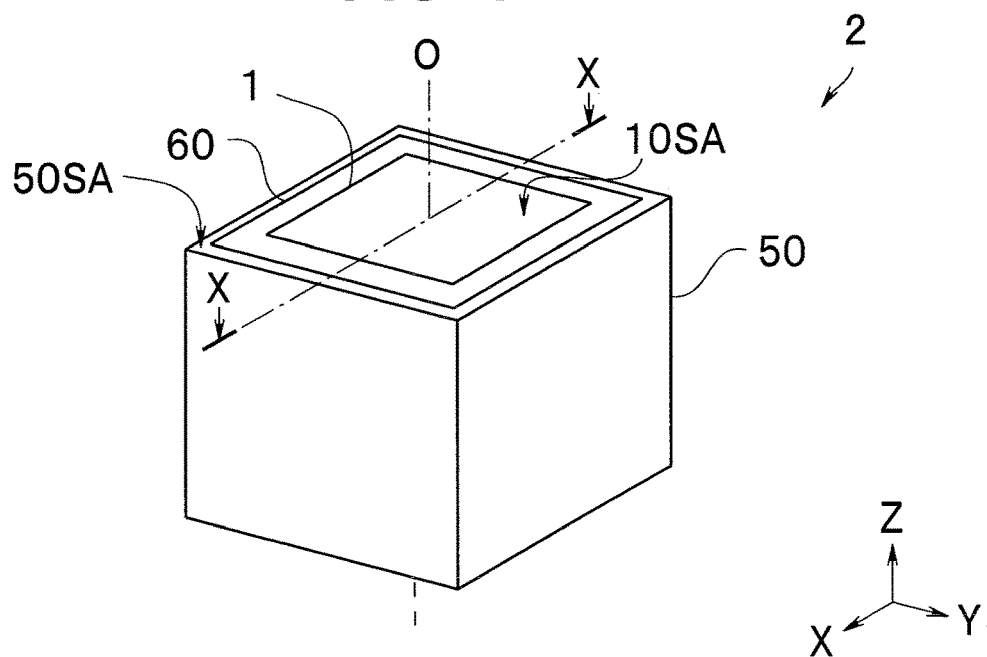
FIG. 9 is a perspective view of the optical unit of the second embodiment.
Figure 10:
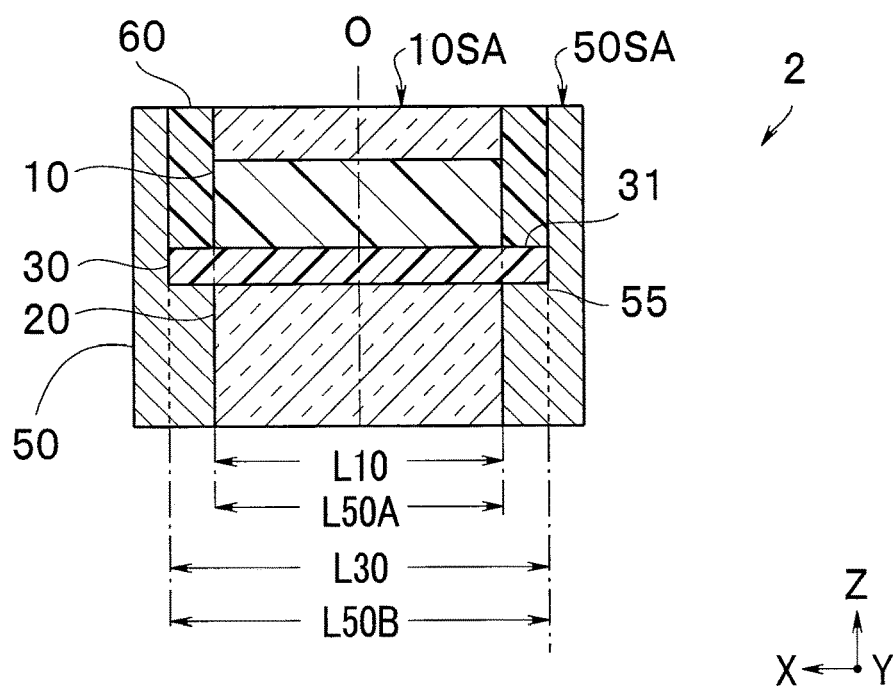
FIG. 10 is a cross-sectional view taken along a line X-X in FIG. 9.

As illustrated in FIGS. 8 to 10, an optical unit 2 of the present embodiment includes the stacked lens 1 of the first embodiment, a frame member (a first frame member) 50, and resin 60 placed to fill a gap between a side surface of the stacked lens 1 and an inner surface of the frame member 50.

The resin 60 fixes the stacked lens 1 to the frame member 50. To block outside light entering a light path through the side surface of the stacked lens 1, it is preferable that the resin 60 be light-blocking resin.

As already described, the stacked lens 1 includes the first optical device 10, the second optical device 20, and the adhesive layer 30. The adhesive layer 30 includes the picture-frame-shaped projection 31 projecting outside the side surfaces of the first optical device 10 and the second optical device 20 with respect to the direction of the optical axis O.

The frame member 50 is a hollow rectangular cylinder having through holes H50, H55. Cross sections of the through holes H50, H55 orthogonal to the optical axis O have a square shape.

As illustrated in FIG. 8, as compared with an inner size L50 of the cross section of the through hole H50 orthogonal to the optical axis O, an inner size L55 of the cross section of the through hole H55 orthogonal to the optical axis O is small. In other words, the through hole H50 has a third projection 55 (hereinafter, referred to as a "projection 55") projecting from an inner surface 50SSA. A wall surface of the projection 55 defines an inner surface of the through hole H55.

Cross sections of the first optical device 10 and the second optical device 20 orthogonal to the optical axis O have a square shape. As illustrated in FIG. 8, an outer size L30 of the adhesive layer 30, which includes the picture-frame-shaped projection 31, is larger than an outer size L1 of the cross sections of the first optical device 10 and the second optical device 20 orthogonal to the optical axis O.

Further, the outer size L30 of the adhesive layer 30 is smaller than the inner size L50 of the through hole 1150 and larger than the inner size L55 of the through hole H55.

Thus, the projection 31 of the adhesive layer 30 of the stacked lens 1 housed in the frame member 50 is in contact with the projection 55 of the frame member 50. The projection 55 is a positioning member (a first positioning member) configured to determine a relative position between the stacked lens 1 and the frame member 50. Thus, in the optical unit 2, the relative position between the stacked lens 1 and the frame member 50 in the optical axis direction is accurately determined. Note that the projection 55 also has an effect to prevent the resin 60 from sticking to the incoming surface of the stacked lens 1.

Figure 6:
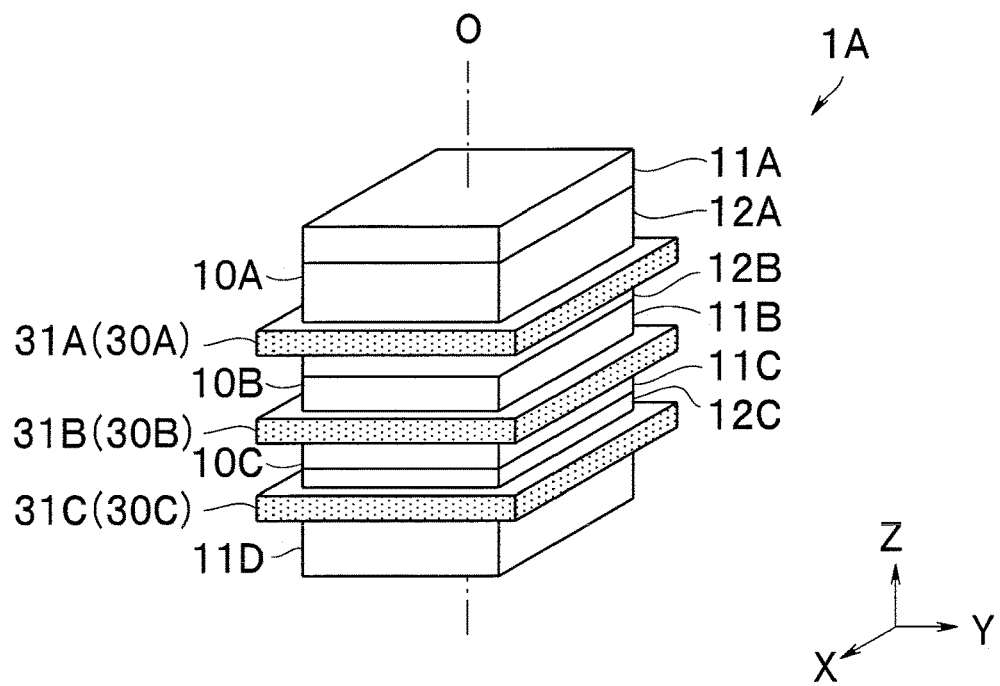
FIG. 6 is a perspective view of a stacked lens of Modification 1 of the first embodiment.

Note that for an optical unit including a stacked lens including two or more adhesive layers each including a projection projecting from a side surface of an optical device as the stacked lens 1A illustrated in FIG. 6, it is sufficient if one projection of a frame member is in contact with one projection of the adhesive layers.

<Method of Manufacturing Optical Unit>

Figure 11:
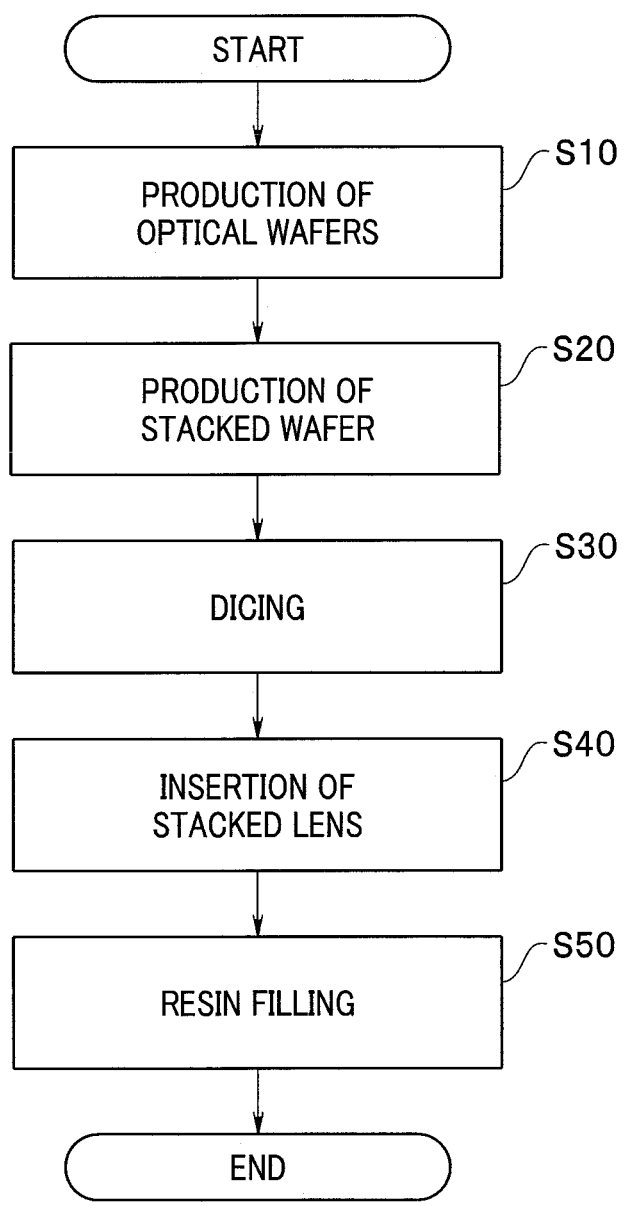
FIG. 11 is a flowchart of a method of manufacturing the optical unit of the second embodiment.

FIG. 11 illustrates a flowchart of a method of manufacturing the optical unit.

<Steps S10 to S30>

It is the same as the method of manufacturing the stacked lens 1 of the first embodiment as already described.

<Step S40> Insertion of Stacked Lens

When each of the plurality of stacked lenses 1, which are produced by dicing the stacked wafer 1W, is inserted into the frame member 50 having the inner surface with the projection 55, the projection 31 of the adhesive layer 30 comes into contact with the projection 55. That is, the projection 55 is the positioning member configured to determine the relative position between the stacked lens 1 and the frame member 50.

<Step S50> Resin Filling

The light-blocking resin 60 is placed to fill a space between an outer peripheral surface (four side surfaces) of the stacked lens 1 and the inner surface of the frame member 50. The resin 60 is subjected to a cure treatment while the first principal surface 10SA is immobilized using, for example, a flat plate so that the first principal surface 10SA of the stacked lens 1 is flush with a top surface 50SA of the frame member 50.

Note that the first principal surface 10SA of the stacked lens 1 and the top surface 50SA of the frame member 50 are not necessarily flush with each other. However, in order to more accurately determine the relative position between the stacked lens 1 and the frame member 50, it is preferable that after positioning using the projection 31 and the projection 55, the soft projection 31 be pressed to deform to make the first principal surface 10SA of the stacked lens 1 flush with the top surface 50SA of the frame member 50 and, in this state, the resin 60 be subjected to the cure treatment.

According to a method of manufacturing the optical unit 2, the relative position between the stacked lens 1 and the frame member 50 is accurately determined by virtue of the use of the projection 31 of the adhesive layer 30, which is easily formed during the manufacturing of the stacked lens 1. Thus, the optical unit 2 is easy to manufacture. The manufacturing method of the present embodiment enables easy manufacturing and reduced manufacturing costs as compared with a conventional manufacturing method including forming, in a side surface of a stacked lens, a recess for positioning.

<Modifications of Second Embodiment>

Since stacked lenses 2A, 2B of Modifications 1, 2 of the second embodiment are similar to the optical unit 2, the same reference sign is assigned to components with the same function and an explanation is omitted.

<Modification 1 of Second Embodiment>

Figure 12:
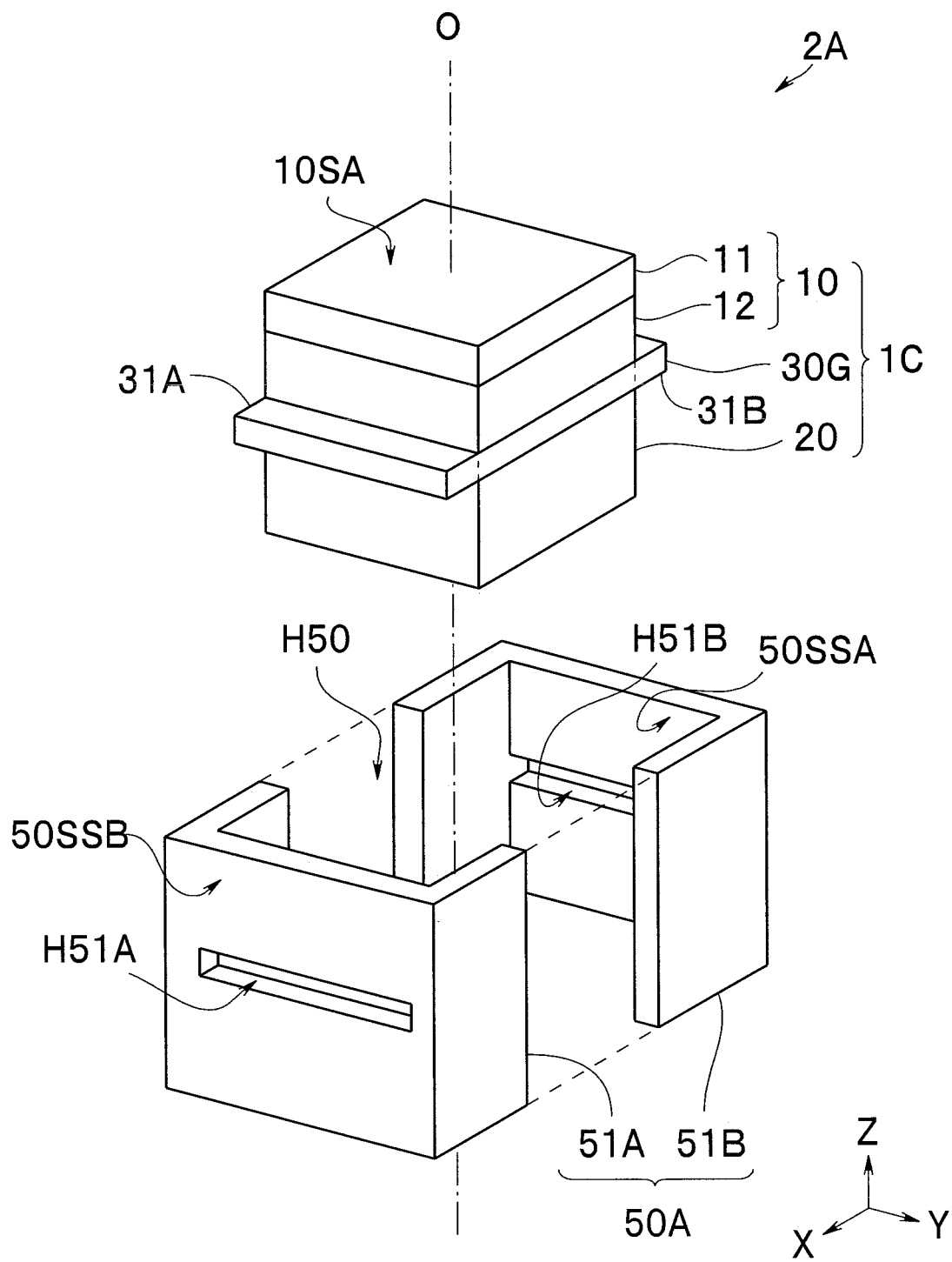
FIG. 12 is an exploded perspective view of an optical unit of Modification 1 of the second embodiment.
Figure 13:
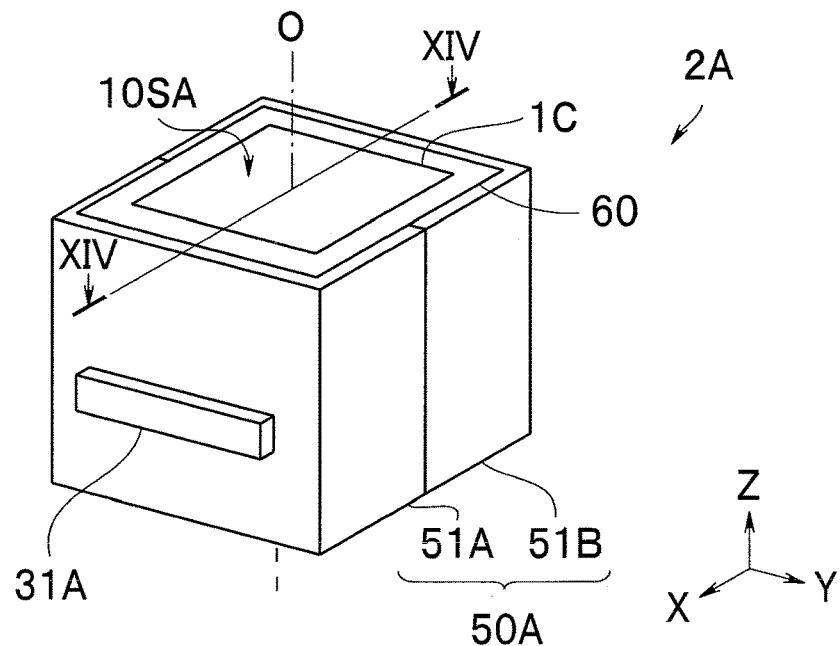
FIG. 13 is a perspective view of the optical unit of Modification 1 of the second embodiment.
Figure 14:
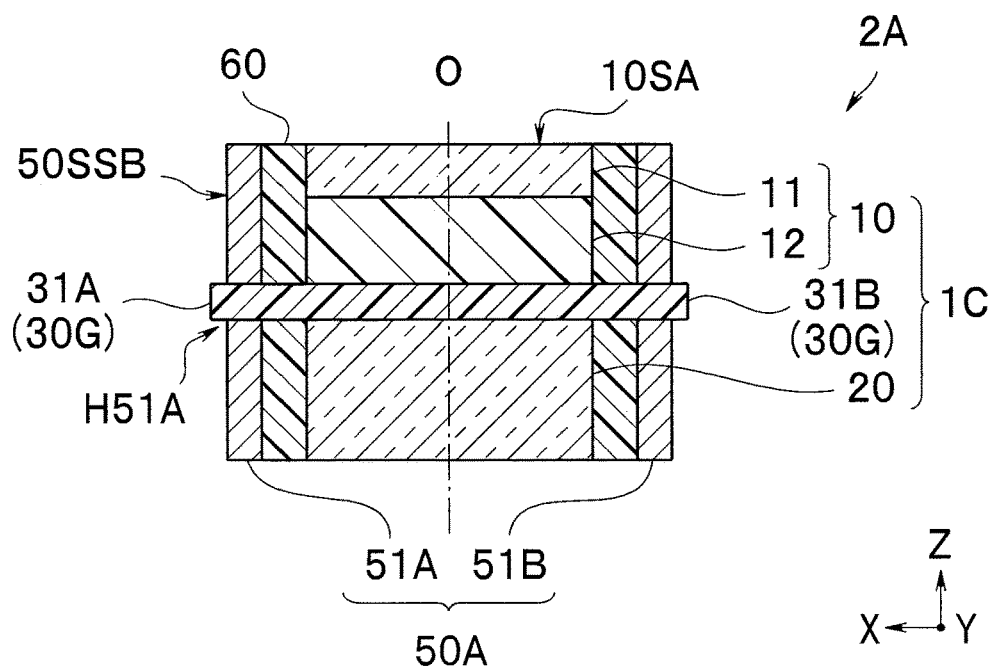
FIG. 14 is a cross-sectional view taken along a line XIV-XIV in FIG. 13.

The optical unit 2A of the present modification illustrated in FIGS. 12 to 14 includes a stacked lens 1C, a frame member 50A, and the resin 60. Note that the resin 60 is not illustrated in FIG. 12.

The stacked lens 1C includes the first optical device 10, the second optical device 20, and an adhesive layer 30G. The first optical device 10 and the second optical device 20 have the same configuration as the configuration of the stacked lens 1 of the first embodiment.

The adhesive layer 30G of the stacked lens 1C includes a projection 31G that is an elongated projection projecting from the side surfaces of the optical devices. The projection 31G includes the two projections 31A, 31B located at the symmetric positions across the optical axis O.

The frame member 50A includes a frame member 51A and a frame member 51B. In the frame member 50A, two through holes H51A, H51B are formed from respective two opposite inner surfaces 50SSA to outer surfaces 50SSB.

An inner size of the two through holes H51A, 1151B is slightly larger than an outer size of the two projections 31A, 31B. The projections 31A, 31B are inserted into the through holes H51A, H51B, respectively.

According to a method of manufacturing the optical unit 2A, the projection 31A of the stacked lens 1C is inserted into the through hole H51A of the frame member 51A. In addition, the projection 31B of the stacked lens 1C is inserted into the through hole H51B of the frame member 51B. That is, the frame member 50A is produced by combining the frame member 51A and the frame member 51B such that the stacked lens 1C is housed.

The through holes H51A, H51B are positioning members configured to determine a relative position between the stacked lens 1C and the frame member 50A.

The optical unit 2A has the same effect as the optical unit 2.

Note that the two projections 31A, 31B projecting from the outer surfaces 50SSB of the optical unit 2A may further be in contact with a second positioning member of another second frame member. The optical unit 2A is easy to be positioned with respect to the second frame member.

<Modification 2 of Second Embodiment>

Figure 15:
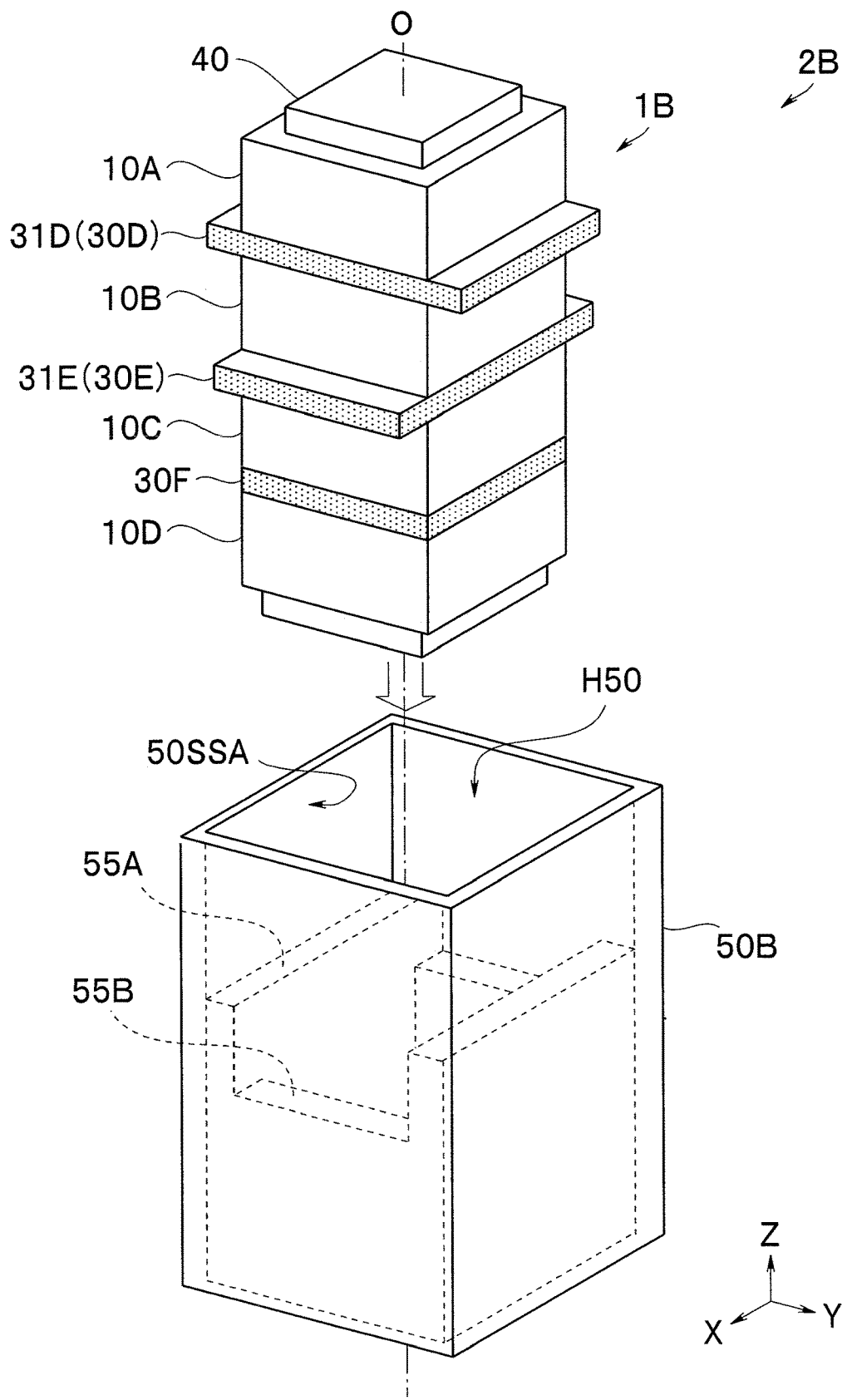
FIG. 15 is an exploded perspective view of an optical unit of Modification 2 of the second embodiment.

The optical unit 2B of the present modification illustrated in FIG. 15 includes the stacked lens 1B and a frame member 50B. As already described, the stacked lens 1B includes the four optical devices 10A to 10D, the three adhesive layers 30D to 30F, and the image pickup device 40.

The first adhesive layer 30D includes the two first projections 31D projecting in the Y-axis direction. The second adhesive layer 30E includes the two second projections 31E projecting in the X-axis direction.

The frame member 50B includes projections 55A, 55B that are positioning members projecting from the inner surface 50SSA of the through hole H50. The projections 55A are located at symmetric positions in the Y-axis direction across the optical axis O. The projections 55B are located at symmetric positions in the X-axis direction across the optical axis O. A plurality of projected images of the two projections 31D and the two projections 31E projected on an imaginary plane orthogonal to the optical axis have no overlap.

When the stacked lens 1B is housed in the through hole H50 of the frame member 50B, the first projections 31D come into contact with the projections 55A and the second projections 31E come into contact with the projections 55B.

Since a relative position between the stacked lens 1B and the frame member 50B is determined by the projections 31D, 31E at the different positions in the optical axis direction and the projections 55A, 55B at the different positions in the optical axis direction, the optical unit 2B is positioned with a higher accuracy than the optical unit 2.

Third Embodiment

Figure 16:
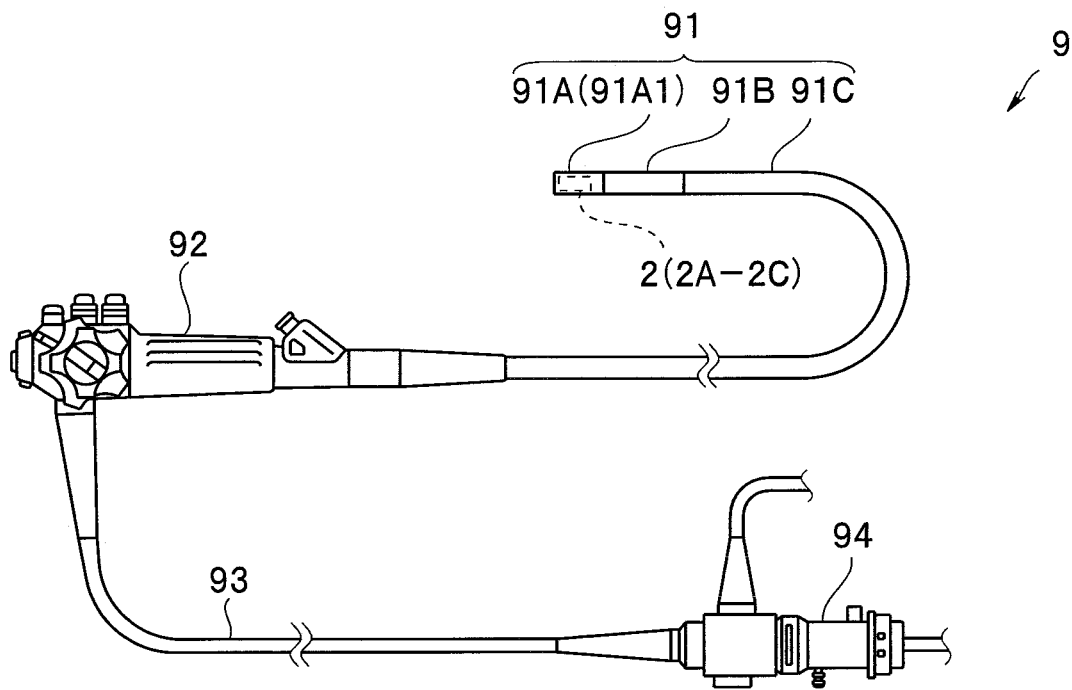
FIG. 16 is an appearance view of an endoscope of a third embodiment.

An endoscope 9 of the present embodiment illustrated in FIG. 16 includes an insertion section 91, an operation section 92, a universal cord 93, and an endoscope connector 94.

The insertion section 91, which is in a form of an elongated tube, is to be inserted into a body cavity of a living body. The insertion section 91, in which a distal end portion 91A, a bending portion 91B, and a flexible tube 91C are disposed continuously in this order from a distal end side, is flexible as a whole.

The distal end portion 91A includes a rigid member 91A1 including various units inside. The various units are an image pickup unit including the optical unit 2 (2A, 2B), a treatment instrument insertion channel, an illumination unit including the optical unit 2 (2A, 2B), and the like.

The bending portion 91B is bendable in upper, lower, right, and left directions in accordance with a rotary operation of a bending knob of the operation section 92 for performing a bending operation.

The flexible tube 91C is a passively flexible tubular member with softness. The treatment instrument insertion channel, various electric signal lines, a light guide fiber bundle, and the like are inserted within the flexible tube 91C. The electric signal lines are drawn from the image pickup unit installed in the distal end portion 91A, being routed to the universal cord 93 through the operation section 92. The light guide fiber bundle is configured to guide light from a light source apparatus, which is an external apparatus, to a distal end surface of the distal end portion 91A.

The operation section 92, which is disposed continuously to a proximal end portion of the insertion section 91, includes a plurality of operation members and the like. The universal cord 93 is a tubular member having flexibility and that is drawn from the operation section 92. The endoscope connector 94 is a connection member for connecting the universal cord 93 and the external apparatus.

The endoscope 9 includes the optical unit 2 (2A, 2B) disposed in the distal end portion 91A of the insertion section 91. As already described, the relative position between the stacked lens and the frame member is accurately determined, so that the optical unit 2 (2A, 2B) is excellent in optical properties.

Note that the optical unit may be housed in a hole of the rigid member 91A1 of the distal end portion 91A or the rigid member 91A1 may be used as a frame member where the stacked lens is housed.

Figure 17:
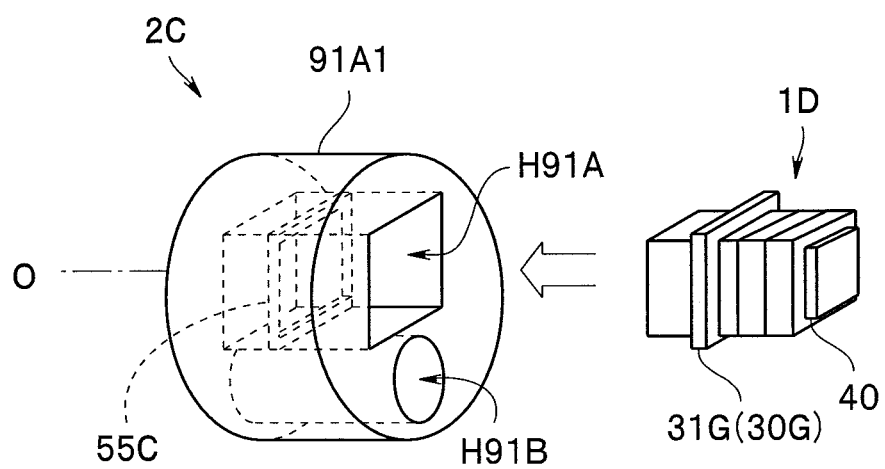
FIG. 17 is an exploded perspective view of the endoscope of the third embodiment.

For example, in an endoscope illustrated in FIG. 17, the rigid member 91A1 (the frame member) and a stacked lens 1D constitute an optical unit 2C. The rigid member 91A1 has a first opening H91A in which the stacked lens 1D is to be housed and a channel opening H91B. An inwardly projecting projection (a positioning member) 55C is formed in an inner surface of the first opening H91A. Note that the projection 55C is in a form of an elongated bank. A hole for housing an illumination optical system and the like, which is not illustrated, is also formed in the rigid member 91A1. The adhesive layer 30G of the stacked lens 1D includes a projection 31G projecting from the side surfaces of the optical devices.

When the stacked lens 1D is inserted into the first opening H91A, the projection 31G of the adhesive layer 30G comes into contact with the projection (the positioning member) 55C. Thus, a relative position between the stacked lens 1D and the distal end portion 91A (the frame member) in the optical axis direction is accurately determined. Thus, the optical unit 2C is excellent in optical properties.

In addition, since machining for forming an engagement portion, such as a recessed portion, in the stacked lens after blade dicing machining is not necessary, the optical unit 2C is easy to manufacture and a reduction in manufacturing costs can be expected. In addition, since the stacked lens 1D is directly attached to the rigid member 91A1, the distal end portion 91A of the endoscope has a small diameter.

Note that the endoscope of the embodiment may be a flexible endoscope including a flexible insertion section or a rigid endoscope including a rigid insertion section. In addition, the endoscope of the embodiment may be used for medical purposes or industrial purposes.

The present invention is not limited to the above-described embodiments and various modifications, improvements, and the like are possible unless the gist of the present invention is changed.

What is claimed is:

1. A stacked lens comprising:
    a first optical device;
    a second optical device disposed on an optical axis of the first optical device; and
    a first adhesive layer bonding the first optical device and the second optical device and including a first projection projecting outside an outer peripheral surface of each of the first optical device and the second optical device, the outer peripheral surface being along the optical axis.

2. The stacked lens according to claim 1, wherein
    the outer peripheral surface includes four side surfaces of each of the first optical device and the second optical device, and
    the first projection projects from at least one of the four side surfaces.

3. The stacked lens according to claim 2, wherein
    the first projection projects from the four side surfaces.

4. The stacked lens according to claim 1, wherein
    the outer peripheral surface of at least one of the first optical device or the second optical device is a cut surface including a striation.

5. The stacked lens according to claim 1, wherein
    at least one of the first optical device or the second optical device is a hybrid lens device including a glass and a resin lens.

6. The stacked lens according to claim 1, wherein
    the adhesive layer is made of transparent resin.

7. The stacked lens according to claim 1, comprising
    an image pickup device configured to receive light collected by the first optical device and the second optical device.

8. The stacked lens according to claim 1, further comprising
    a third optical device and a second adhesive layer bonding the second optical device and the third optical device, wherein
    the second adhesive layer includes a second projection, the second projection projecting outside the outer peripheral surface of the second optical device, the outer peripheral surface being along the optical axis, the second projection projecting outside an outer peripheral surface of the third optical device, the outer peripheral surface being along the optical axis, and
    a projected image of the first projection and a projected image of the second projection that are projected on an imaginary plane orthogonal to the optical axis have no overlap.

9. An optical unit comprising:
    a stacked lens including: a first optical device; a second optical device disposed on an optical axis of the first optical device; and a first adhesive layer bonding the first optical device and the second optical device and including a first projection projecting outside an outer peripheral surface of each of the first optical device and the second optical device, the outer peripheral surface being along the optical axis; and
    a first frame member in which the stacked lens is housed and that has an inner surface including a first positioning member, the first projection being in contact with the first positioning member.

10. The optical unit according to claim 9, wherein
    the first positioning member includes a third projection projecting from the inner surface.

11. The optical unit according to claim 9, wherein
    the first positioning member includes a through hole from the inner surface to an outer surface of the first frame member and through which the first projection penetrates.

12. The optical unit according to claim 9, further comprising
    a second frame member including a second positioning member being in contact with the first projection projecting from an outer surface of the first frame member.

13. The optical unit according to claim 9, wherein
    the stacked lens further includes a third optical device disposed on the optical axis of the first optical device and a second adhesive layer bonding the second optical device and the third optical device,
    the second adhesive layer includes a second projection, the second projection projecting outside the outer peripheral surface of the second optical device, the outer peripheral surface being along the optical axis, the second projection projecting outside an outer peripheral surface of the third optical device, the outer peripheral surface being along the optical axis,
    a projected image of the first projection and a projected image of the second projection that are projected on an imaginary plane orthogonal to the optical axis have no overlap, and the first frame member includes a plurality of positioning members, the plurality of positioning members each being in contact with the first projection or the second projection.

14. An endoscope comprising an insertion section and an optical unit disposed in a distal end portion of the insertion section, the optical unit including:

a stacked lens including: a first optical device; a second optical device disposed on an optical axis of the first optical device; and a first adhesive layer bonding the first optical device and the second optical device and including a first projection projecting outside an outer peripheral surface of each of the first optical device and the second optical device, the outer peripheral surface being along the optical axis; and a frame member in which the stacked lens is housed and that has an inner surface including a positioning member, the first projection being in contact with the positioning member.

15. A method of manufacturing an optical unit, the method comprising:

producing a stacked wafer including a first optical wafer including a plurality of first optical devices, a second optical wafer including a plurality of second optical devices, and an adhesive layer between the first optical wafer and the second optical wafer;

cutting the stacked wafer using a dicing blade to produce a stacked lens, the stacked lens including one of the first optical devices, one of the second optical devices, and a first adhesive layer including a projection projecting outside a cut surface; and housing the stacked lens in a frame member having an inner surface including a positioning member in a state where the projection is in contact with the positioning member.

16. The method of manufacturing an optical unit according to claim 15, the method comprising placing resin to fill a space between a side surface of the stacked lens and the inner surface of the frame member.

17. The method of manufacturing an optical unit according to claim 15, the method comprising:

disposing an image pickup device in the stacked wafer before the cutting of the stacked wafer; and cutting the stacked wafer in a state where the stacked lens includes the image pickup device.

* * * * *